US012661078B2

(12) United States Patent
M et al.

(10) Patent No.: US 12,661,078 B2
(45) Date of Patent: Jun. 23, 2026

(54) METHOD, DEVICE, AND SYSTEM FOR DETERMINING ABNORMALITY IN MYOCARDIUM REGION

(71) Applicant: Siemens Healthcare GmbH, Erlangen (DE)

(72) Inventors: Muniraju M, Bengaluru (IN); Laxmikanta Shanbhag, Bengaluru (IN)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/393,524

(22) Filed: Aug. 4, 2021

(65) Prior Publication Data

US 2022/0039769 A1      Feb. 10, 2022

(30) Foreign Application Priority Data

Aug. 4, 2020   (EP) ..................................... 20189358

(51) Int. Cl.
*A61B 6/50*          (2024.01)
*A61B 6/00*          (2006.01)
(Continued)

(52) U.S. Cl.
CPC .............. *A61B 6/507* (2013.01); *A61B 6/504* (2013.01); *A61B 6/5247* (2013.01); *A61B 8/06* (2013.01); *A61B 8/0891* (2013.01); *A61B 8/5261* (2013.01)

(58) Field of Classification Search
CPC . G06T 2207/10081; G06T 2207/10088; G06T 2207/10121; G06T 2207/10132;
(Continued)

(56) References Cited

U.S. PATENT DOCUMENTS 5,151,856 A * 9/1992 Halmann ................ G06T 15/00
600/410
10,987,010 B2 * 4/2021 Grady .................. A61B 5/7275
(Continued)

FOREIGN PATENT DOCUMENTS

CN        110070534 A      7/2019
EP         3071109 A1     9/2016
(Continued)

OTHER PUBLICATIONS

European Search Report for European Application No. 20189358. 3-1210 dated Jan. 29, 2021.
(Continued)

*Primary Examiner* — Bo Joseph Peng
(74) *Attorney, Agent, or Firm* — Lempia Summerfield Katz LLC

(57) ABSTRACT

A method, device, and system for determining at least one blood vessel contributing to an abnormality in a myocardium region are provided. The method includes receiving from a medical imaging device a medical image associated with the myocardium region. The method further includes identifying from the medical image a region of abnormality in the myocardium region. Additionally, the method includes generating a simulation of a plurality of blood vessels associated with the myocardium region. The method includes determining from the simulation of the plurality of blood vessels at least one blood vessel contributing to the abnormality in the myocardium region. The at least one blood vessel is associated with the region of abnormality in the myocardium region.

18 Claims, 6 Drawing Sheets

(51) Int. Cl.

| | | |
|---|---|---|
| *A61B 8/00* | (2006.01) | |
| *A61B 8/06* | (2006.01) | |
| *A61B 8/08* | (2006.01) | |

(58) Field of Classification Search
CPC ............. G06T 2207/20128; G06T 7/11; G06T 2207/30048; G06T 2207/30101; G06T 7/0012; A61B 6/507; A61B 6/504; A61B 6/5247; A61B 8/06; A61B 8/0891; A61B 8/5261

See application file for complete search history.

(56) References Cited

U.S. PATENT DOCUMENTS

| | | | |
|---|---|---|---|
| 2005/0272992 A1* | 12/2005 | O'Donnell | ................ G06T 7/12 |
| | | | 600/407 |
| 2007/0165917 A1 | 7/2007 | Cao | |
| 2010/0296709 A1 | 11/2010 | Ostrovsky-berman | |
| 2011/0235878 A1 | 9/2011 | Nakayama | |
| 2012/0041324 A1* | 2/2012 | Taylor | .................. A61B 5/1075 |
| | | | 702/19 |
| 2014/0355858 A1* | 12/2014 | O'Dell | ...................... G06T 7/11 |
| | | | 382/131 |
| 2015/0139394 A1* | 5/2015 | Kang | .................... A61B 6/542 |
| | | | 378/62 |
| 2015/0374243 A1* | 12/2015 | Itu | ...................... A61B 5/7275 |
| | | | 703/2 |
| 2016/0180042 A1* | 6/2016 | Menon | ................. A61B 5/0042 |
| | | | 705/2 |
| 2019/0380593 A1 | 12/2019 | Bouwman et al. | |
| 2020/0105420 A1* | 4/2020 | Malota | ................... G16H 30/20 |

FOREIGN PATENT DOCUMENTS

| | | | |
|---|---|---|---|
| JP | 2004181176 A | * | 7/2004 |
| JP | 2014004149 A | * | 1/2014 |
| WO | 2007061931 A2 | | 5/2007 |
| WO | 2015/076551 A1 | | 5/2015 |

OTHER PUBLICATIONS

Hamo, Carine E et al., "The Systematic Evaluation of Identifying the Infarct Related Artery Utilizing Cardiac Magnetic Resonance in Patients Presenting with ST-Elevation Myocardial Infarction," PLOS One, vol. 12, Jan. 6, 2017, pp. 1-12.

Heitner John F. et al., "Identifying the Infarct-Related Artery in Patients With Non-ST-Segment-Elevation Myocardial Infarction," Circulation: Cardiovascular Interventions, vol. 12, No. 5, 2019, pp. 1-10.

Rudyanto, Rina D et al., "Comparing algorithms for automated vessel segmentation in computed tomography scans of the lung: the VESSEL12 study," Medical Image Analysis, vol. 18 (2014), pp. 1-42.

Xunlei, Wu et al., "Segmentation and reconstruction of vascular structures for 3D real-time simulation," Medical Image Analysis; vol. 15, Feb. 2011, pp. 22-34.

* cited by examiner

METHOD, DEVICE, AND SYSTEM FOR DETERMINING ABNORMALITY IN MYOCARDIUM REGION

PRIORITY

This application claims the benefit of European Patent Application Number EP 20189358.3, filed on Aug. 4, 2020, which is hereby incorporated by reference in its entirety.

FIELD OF TECHNOLOGY

The present embodiments relate to a method, device, and system for determining abnormality in myocardium region. In particular, the present embodiments relate to a method, device, and system for determining a blood vessel contributing to an abnormality in a myocardium region.

BACKGROUND

Perfusion is passage of fluid through circulatory system or lymphatic system to an organ or tissue. Perfusion is an important phenomenon for supply of blood to capillary bed in tissues and organs. Poor perfusion, or ischemia, may result in multiple complications such as coronary heart disease, deep vein thrombosis, etc. Medical imaging based perfusion studies of myocardium are used for diagnosis of abnormalities in myocardium such as myocardium ischemia, myocardial infarction, myocardial thickening, etc. The perfusion studies provide information related to perfused region in the myocardium. However, the perfusion study may not readily provide information regarding which coronary artery may be contributing to the underlying abnormality in the myocardium region. Perfusion studies may require a physician to manually identify one or more coronary arteries that may be contributing to ischemia.

Currently, there is no way of automatically detecting blood vessels that may contribute to an abnormality in the myocardium region during the evaluation of perfusion.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method, a device, and a system that enable automatic determination of one or more blood vessels contributing to a region of abnormality in a myocardium region that is accurate is provided.

In one aspect, a method of determining at least one blood vessel contributing to an abnormality in a myocardium region is provided. The method includes receiving a medical image associated with the myocardium region. The medical image may be received from a medical imaging device configured to acquire a plurality of medical images associated with a patient. The medical imaging device may include, for example, but not limited to, a computed tomography device, a magnetic resonance imaging device, an X-ray imaging device, an ultrasound imaging device, etc. The medical image may include one or more objects associated with the patient. The objects may be, for example, the myocardium region associated with the patient. The method further includes identifying from the medical image a region of abnormality in the myocardium region. The abnormality may be caused due to poor perfusion or ischemia in the myocardium region. The abnormality may be, for example, myocardium infarction, or any other cardiac disease.

The method further includes generating a simulation of a plurality of blood vessels associated with the myocardium region. The simulation may be generated, for example, using a simulation model. The simulation may include, for example, a 3-dimensional model of the plurality of the blood vessels associated with the myocardium region. Simulating the blood vessels enables identification of at least one blood vessel that may be contributing to the abnormality in the myocardium region. The method further includes determining from the simulated blood vessels at least one blood vessel contributing to the abnormality in the myocardium region. In an embodiment, the at least one blood vessel may be associated with the region of abnormality in the myocardium region. In one embodiment, the present embodiments enable accurate identification of the at least one blood vessel contributing to the abnormality in the myocardium region. Therefore, manual acts of identifying the at least one blood vessel is eliminated.

According to an embodiment, identifying the region of abnormality in the myocardium region includes obtaining from a medical database medical data associated with the myocardium region. The medical data may include, for example, geometrical representation of the myocardium region, a plurality of image segmentation information associated with the myocardium region, etc. The image segmentation information may further be associated with at least one nomenclature for the segments in the myocardium region. In an embodiment, the image segmentation information may be a standard segmentation information associated with the myocardium region. The method further includes determining from the medical image a point of abnormality. In an embodiment, the medical image may depict a point of abnormality in the myocardium region based on one or more perfusion details associated with the imaged myocardium region. For example, the region of the myocardium region with poor perfusion may appear different over the region with advanced/optimum perfusion.

The method further includes mapping the point of abnormality in the medical image with the medical data associated with the myocardium region. Mapping the point of abnormality with the medical data enables accurate identification of the region of abnormality in the myocardium region. For example, the point of abnormality may lie within a specific region of the myocardium. Mapping may include, for example, mapping the point of abnormality identified from the medical image on to the geometric representation of the myocardium obtained from the medical database. In an embodiment, the medical image may also include anatomical information related to an imaged region of the myocardium. The anatomical information of the imaged region further enables accurate mapping of the point of abnormality in the myocardium region with the geometric representation of the myocardium from the medical database. The method further includes determining the region of abnormality in the myocardium based on the mapping. In one embodiment, effective and accurate determination of an affected region in the myocardium is enabled. Therefore, any error in treatment process is avoided.

According to another embodiment, generating the simulation of the plurality of blood vessels includes determining the plurality of blood vessels associated with the myocardium region. The plurality of the blood vessels may be determined, for example, from the standard medical data obtained from the medical database. The plurality of blood vessels may be known to be associated with the myocardium region. The plurality of blood vessels may include, for example, left anterior descending artery (LAD), right coronary artery (RCA), left circumflex artery (LCX), etc. The method further includes generating a virtual model of the plurality of the blood vessels associated with the myocardium region. The virtual model may be a simulation model of the plurality of the blood vessels. The virtual model provides information related to the blood vessels that may be associated with the region of abnormality in the myocardium region.

According to an embodiment, generating the simulation of the plurality of blood vessels further includes generating a mask overlay on the plurality of the blood vessels determined to be associated with the myocardium region. For example, a mask is overlaid on the determined blood vessels such that background image information in the medical data is avoided. The overlay of the mask may generate a negative cast of the myocardium and the associated plurality of the blood vessels. The mask overlay enables accurate segmentation of the plurality of the blood vessels while avoiding the background image information. The method further includes segmenting the plurality of blood vessels determined from the mask overlay. The segmented blood vessels may be used for the generation of the virtual model of the blood vessels. In one embodiment, effective segmentation of the plurality of blood vessels enables accurate construction of the virtual model of the blood vessels.

According to another embodiment, the method further includes determining a centerline associated with each blood vessel of the plurality of blood vessels. The centerline of the blood vessel is a medial axis along the tubular structure of the blood vessel. The centerline of the blood vessel enables determining a vascular length of the blood vessel. The method further includes determining a distal end of each of the blood vessel. The distal end of the blood vessel may be the end furthest away from the myocardium region. The method further includes generating one or more voxels originating from the distal end of each of the blood vessels. In an embodiment, the one or more voxels may be generated based on one or more neighboring voxels surrounding the centerline of the distal end of the blood vessels. In a further embodiment, the one or more voxels may be generated using a region growing algorithm and a region merging algorithm. The one or more voxels may be generated and added to the distal end of the blood vessels such that a proximal end of each of the blood vessels reach/connect with the myocardium region. The method further includes generating the virtual model of the plurality of the blood vessels based on the generated voxels. In one embodiment, the generated virtual model of the blood vessels includes the distal end and the proximal end. Further, the virtual model is constructed such that the proximal end of the generated blood vessels connects with the myocardium region in the medical image. Therefore, determination of the at least one blood vessel contributing to the abnormality in the myocardium region is accurately enabled.

According to yet another embodiment, determining the at least one blood vessel contributing to the abnormality in the myocardium region includes comparing the medical data associated with the myocardium region with the simulated plurality of blood vessels. The comparison is performed to match the medical data and the simulated blood vessels. The medical data may include one or more standard details associated with the blood vessels connected to the myocardium region. The comparison of the medical data with the simulated blood vessels enables accurate determination of which of the plurality of blood vessels is connected to the myocardium region in the medical image. The method further includes determining from the comparison the at least one blood vessel connecting to the region of abnormality in the myocardium region. In one embodiment, accurate determination of the at least one blood vessel contributing to the abnormality enables timely determination of next course of medical action to be taken for the patient. Therefore, undue delay in proceeding with further medical procedure is avoided. Additionally, the manual effort of perusing through the medical data to determine the blood vessel causing the abnormality in the myocardium region is avoided.

According to an embodiment, the medical image is a 3-dimensional medical image. Therefore, volume information associated with the myocardium and the blood vessels may be obtained.

According to yet another embodiment, the medical image is at least one of a computed tomography image, X-ray fluoroscopic image, magnetic resonance imaging based image, and ultrasound image.

A medical imaging device for determining at least one blood vessel contributing to an abnormality in a myocardium region is also provided. The device includes one or more processing units, a scanner unit configured to capture one or more medical images, and a memory coupled to the one or more processing units. The memory includes a module that is configured to perform the method acts as described above.

A system for determining at least one blood vessel contributing to an abnormality in a myocardium region is provided. According to an embodiment, the system includes one or more servers, a medical imaging device coupled to the one or more servers. The one or more servers include one or more instructions that, when executed, cause the one or more servers to perform the method acts as described above.

The present embodiments relate, in one aspect, to a computer program product including a computer program. The computer program is loadable into a storage unit of a system and includes program code sections to make the system execute the method according to an aspect of the present embodiments when the computer program is executed in the system.

The present embodiments relate, in one aspect, to a computer-readable medium (e.g., non-transitory computer-readable storage medium), on which program code sections of a computer program are saved. The program code sections are loadable into and/or executable in a system to make the system execute the method according to an aspect of the present embodiments when the program code sections are executed in the system.

The realization of the present embodiments by a computer program product and/or a computer-readable medium has the advantage that already existing management systems may be easily adopted by software updates in order to work as proposed by the present embodiments.

The computer program product may be, for example, a computer program or include another element apart from the computer program. This other element may be hardware (e.g., a memory device), on which the computer program is stored, a hardware key for using the computer program and the like, and/or software (e.g., a documentation or a software key for using the computer program).

BRIEF DESCRIPTION OF THE DRAWINGS

FIG. 5 illustrates a flowchart of a method of generating a simulation of the plurality of blood vessels, according to an embodiment.

FIG. 6 illustrates a flowchart of a method of determining the at least one blood vessel contributing to the abnormality in the myocardium region, according to an embodiment.

DETAILED DESCRIPTION

Figure 1:
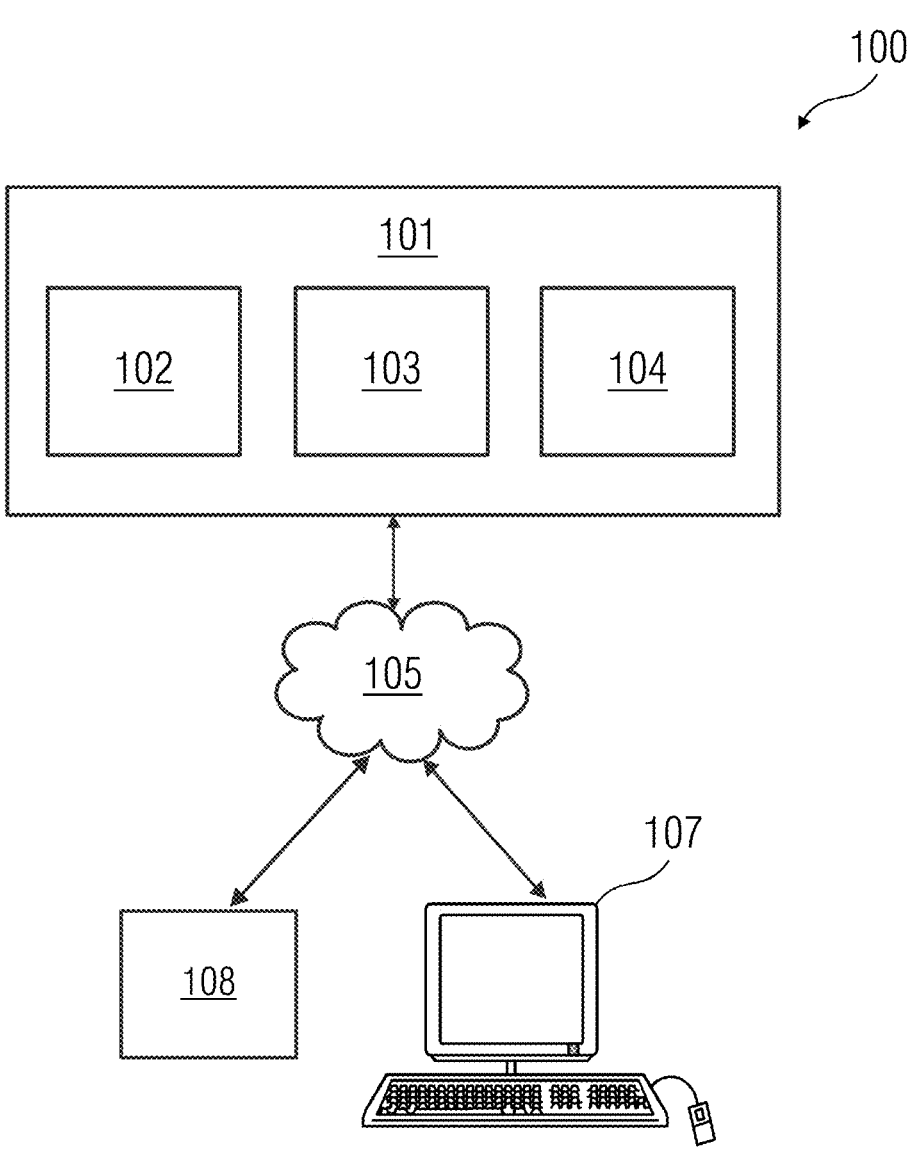
FIG. 1 illustrates a block diagram of a client-server architecture that provides a geometric modeling of components representing different parts of a real-world object, according to an embodiment.

Hereinafter, embodiments are described in detail. The various embodiments are described with reference to the drawings, where like reference numerals are used to refer to like elements throughout. In the following description, for purpose of explanation, numerous specific details are set forth in order to provide a thorough understanding of one or more embodiments. It may be evident that such embodiments may be practiced without these specific details.

FIG. 1 provides an illustration of a block diagram of a client-server architecture that is a geometric modelling of components representing different parts of real-world objects, according to an embodiment. The client-server architecture 100 includes a server 101 and a plurality of client devices 107. Each of the client device 107 is connected to the server 101 via a network 105 (e.g., local area network (LAN), wide area network (WAN), WiFi, etc.). In one embodiment, the server 101 is deployed in a cloud computing environment. As used herein, "cloud computing environment" refers to a processing environment including configurable computing physical and logical resources (e.g., networks, servers, storage, applications, services, etc.) and data distributed over the network 105 (e.g., the Internet). The cloud computing environment provides on-demand network access to a shared pool of the configurable computing physical and logical resources. The server 101 may include a medical database 102 that includes medical images and associated medical datasets related to one or more patients that is maintained by a healthcare service provider. The medical database 102 may further include medical data associated with the myocardium region. The medical data may further be associated with nomenclature and segmentation information associated with the myocardium region and a plurality of blood vessels. The server 101 may include a module 103 that is configured to determine at least one blood vessel contributing to an abnormality in the myocardium region. Additionally, the server 101 may include a network interface 104 for communicating with the client device 107 via the network 105.

The client device 107 is a user device used by a user (e.g., medical personnel). In an embodiment, the user device 107 may be used by the user to receive data associated with at least one blood vessel contributing to the abnormality in the myocardium region. The image may be accessed by the user via a graphical user interface of an end user web application on the user device 107. In another embodiment, a request may be sent to the server 101 to access the information associated with the at least one blood vessel via the network 105. A device 108 may be connected to the server 101 through the network 105. The device 108 may be a medical imaging device 108 capable of acquiring a plurality of medical images. The medical imaging device 108 may be, for example, a computed tomography imaging unit, an X-ray fluoroscopy imaging unit, a magnetic resonance imaging unit, an ultrasound imaging unit, etc.

Figure 2:
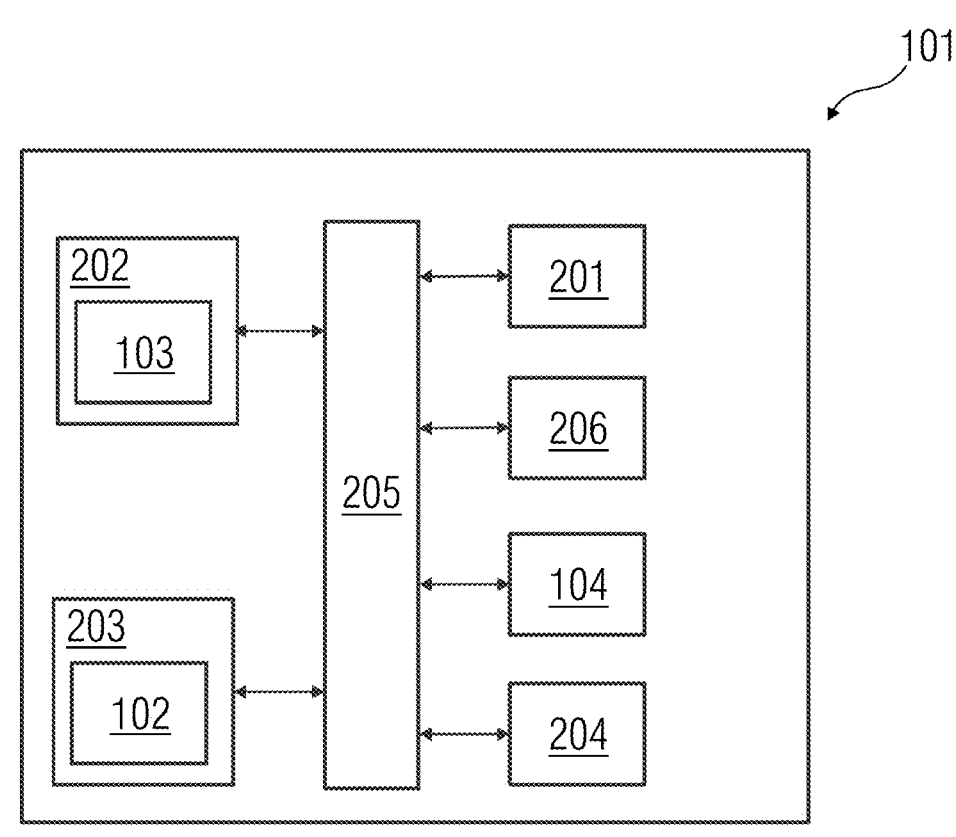
FIG. 2 illustrates a block diagram of a data processing system in which an embodiment for determining a blood vessel contributing to an abnormality in a myocardium region may be implemented.

FIG. 2 is a block diagram of a data processing system 101 in which an embodiment may be implemented, for example, as a system 101 for determining a blood vessel contributing to an abnormality in a myocardium region, configured to perform the processes as described therein. The server 101 is an exemplary implementation of the system in FIG. 2. In FIG. 2, the data processing system 101 includes a processing unit 201, a memory 202, a storage unit 203, an input unit 204, an output unit 206, a bus 205, and the network interface 104.

The processing unit 201, as used herein, provides any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 201 may also include embedded controllers, such as generic or programmable logic devices or arrays, application specific integrated circuits, single-chip computers, and the like.

The memory 202 may be volatile memory and non-volatile memory. The memory 202 may be coupled for communication with the processing unit 201. The processing unit 201 may execute instructions and/or code stored in the memory 202. A variety of computer-readable storage media may be stored in and accessed from the memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 202 includes a module 103 stored in the form of machine-readable instructions on any of the above-mentioned storage media and may be in communication to and executed by processor 201. When executed by the processor 201, the module 103 causes the processor 201 to determine at least one blood vessel contributing to an abnormality in the myocardium region. Method acts executed by the processor 201 to achieve the abovementioned functionality are elaborated upon in detail in FIGS. 3, 4, 5 and 6.

The storage unit 203 may be a non-transitory storage medium that stores a medical database 102. The medical database 102 is a repository of medical images and associated medical datasets related to one or more patients that is maintained by a healthcare service provider. The medical database 102 may further include medical data associated with the myocardium region. The medical data may further be associated with nomenclature and segmentation information associated with the myocardium region and a plurality of blood vessels. The input unit 204 may include an input device such as, for example, a keypad, a touch-sensitive display, a camera (e.g., a camera receiving gesture-based inputs), etc. capable of receiving input signal such as a medical image. The bus 205 acts as interconnect between the processor 201, the memory 202, the storage unit 203, the input unit 204, the output unit 206, and the network interface 104.

Those of ordinary skilled in the art will appreciate that the hardware depicted in FIG. 1 may vary for particular implementations. For example, other peripheral devices such as, for example, an optical disk drive and the like, a Local Area Network (LAN)/Wide Area Network (WAN)/Wireless (e.g., Wi-Fi) adapter, a graphics adapter, a disk controller, and an input/output (I/O) adapter may also be used in addition or in place of the hardware depicted. The depicted example is provided for the purpose of explanation only and is not meant to imply architectural limitations with respect to the present disclosure.

A data processing system 101 in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through a pointing device. The position of the cursor may be changed and/or an event such as clicking a mouse button, generated to actuate a desired response.

Disclosed embodiments provide systems and methods for determining abnormality in the myocardium region. For example, the systems and methods may determine a blood vessel contributing to the abnormality in the myocardium region.

Figure 3:
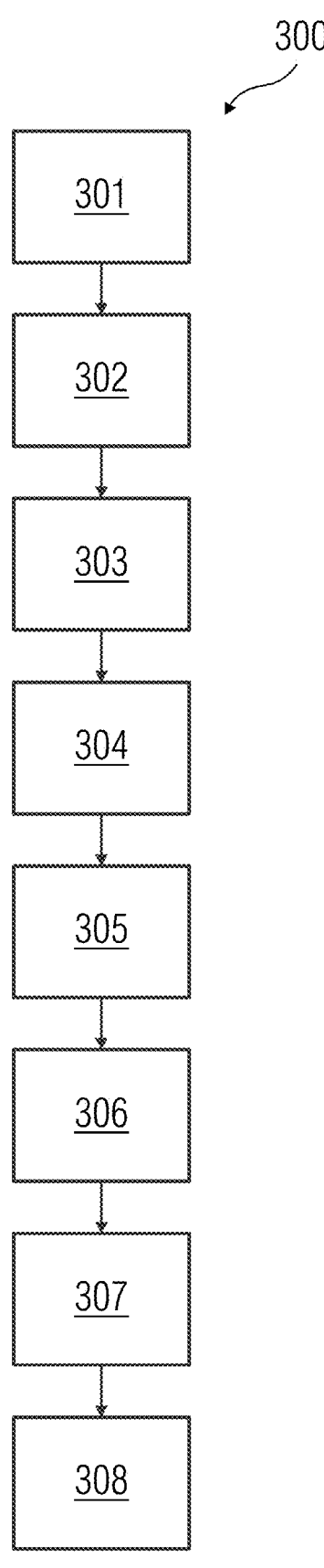
FIG. 3 illustrates a flowchart of a method of determining at least one blood vessel contributing to an abnormality in a myocardium region, according to an embodiment.

FIG. 3 illustrates a flowchart of a method 300 of determining at least one blood vessel contributing to an abnormality in a myocardium region, according to an embodiment. The method 300 includes act 301 of receiving a medical image from a medical imaging device. The medical imaging device may include a computed tomography unit, an X-ray fluoroscopy imaging unit, a magnetic resonance imaging unit, a PET imaging unit, an ultrasound imaging unit, or any other radiological imaging device. The medical image includes imaging information associated with a patient. The imaging information may include, for example, the myocardium region associated with a patient. At act 302, a region of abnormality in the myocardium region is identified from the medical image. The region of abnormality may indicate a presence of ischemia in the myocardium region (e.g., a region of poor perfusion). The region of abnormality may be identified, for example, based on a difference in a contrast uptake in a specific region in the myocardium in comparison with a contrast update in other regions of the myocardium.

At act 303, a simulation of a plurality of blood vessels is generated, where the plurality of blood vessels are associated with the myocardium region. The plurality of blood vessels may supply blood to the myocardium region for effective functioning of the myocardium. In an embodiment, the simulation of the plurality of the blood vessels may be generated using a simulation model. The simulation enables determination of the blood vessels that may supply blood to the myocardium region. At act 304, a centerline associated with each blood vessel of the plurality of the blood vessels is determined. The centerline of the blood vessels enables effective determination of vascular length of the blood vessels. The simulated blood vessels may present a virtual representation of the blood vessels. Further, it is to be determined which of the simulated blood vessels contribute to the abnormality in the myocardium region. Therefore, the simulated blood vessels may be connected to the myocardium region in the medical image in order to determine the blood vessel contributing to the abnormality. At act 305, a distal end of the centerline of each of the blood vessel is identified. The distal end of the blood vessel may be the farthest point of the blood vessel from the myocardium region. From the distal end of the centerline of each blood vessel, one or more voxels may be generated at act 306. The one or more voxels may be generated such that a proximal end of each of the blood vessel is generated, thereby connecting the simulated blood vessels to the myocardium region. The one or more voxels generated from the distal end of the centerline may be based on a plurality of voxels surrounding the distal end of the blood vessels. In an embodiment, a region growing algorithm and/or a region merging algorithm may be used for generation of the one or more voxels. The region growing algorithm may use the surrounding voxels to generate and add new voxels to a region if no edges are detected.

At act 307, a virtual model of the plurality of the blood vessels is generated based on the generated one or more voxels. The virtual model of the plurality of the blood vessels may be such that the proximal end of the blood vessels connects to the myocardium region identified in the medical image. At act 308, at least one blood vessel contributing to the region of abnormality in the myocardium region is determined from the generated virtual model. In an embodiment, the at least one blood vessel may be the blood vessel that supplies blood to the region of abnormality in the myocardium region.

Figure 4:
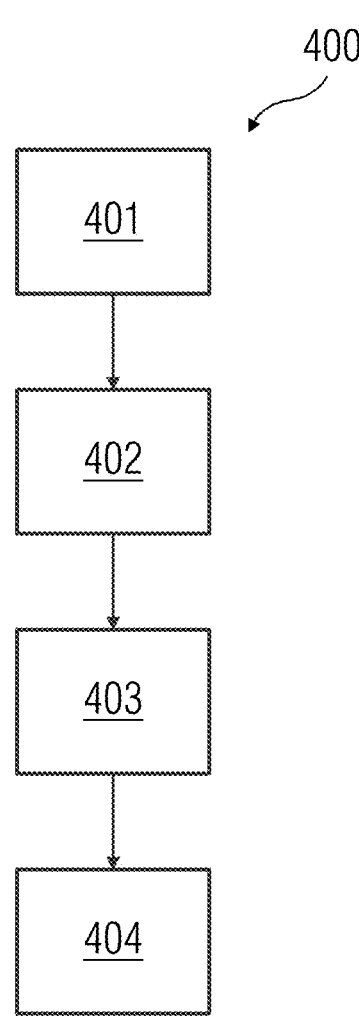
FIG. 4 illustrates a flowchart of a method of identifying the region of abnormality in the myocardium region, according to an embodiment.

FIG. 4 illustrates a flowchart of a method 400 of identifying the region of abnormality in the myocardium region. At act 401, medical data associated with the myocardium region is obtained from the medical database 102. The medical data may include, for example, geometric information associated with myocardium region. The geometric information may be standard information associated with myocardium, which may be used as a reference. Additionally, the medical data includes image segmentation information and nomenclature information associated with plurality of blood vessels associated with the myocardium region. The method 400 further includes act 402 of determining from the medical image a point of abnormality. The point of abnormality may be a point on the myocardium region in the medical image that may appear to be abnormal in comparison to surrounding region of the myocardium. For example, the point of abnormality may have a different contrast uptake in comparison to a surrounding region of the point of abnormality. At act 403, the point of abnormality in the medical image is mapped with the medical data associated with the myocardium region. Mapping of the abnormal point in the medical image enables accurate determination of the region of abnormality in the myocardium region. At act 404, the region of abnormality in the myocardium region is identified based on the mapping. Additionally, mapping of the point of abnormality provides a 3-dimensional representation of the region of abnormality in the myocardium region.

Figure 5:
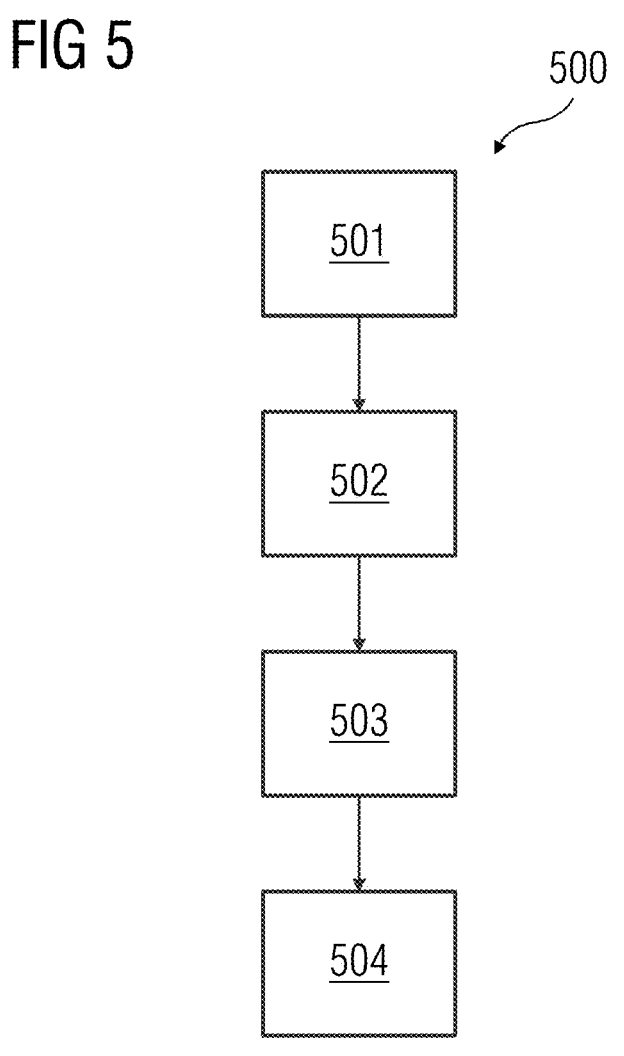

FIG. 5 illustrates a flowchart of a method 500 of generating the simulation of the plurality of blood vessels, according to an embodiment. At act 501, the plurality of blood vessels associated with the myocardium region are determined from the medical data associated with the myocardium region. At act 502, a mask overlay is generated on the plurality of blood vessels. Masking is an image processing technique in which pixel/voxel intensity of a portion image is changed to zero. The overlay of the mask on the plurality of blood vessels may generate a negative cast of the myocardium region and associated background image information in the medical image. The masking of the blood vessels may be performed using one or more methods known in the art. At act 503, the masked plurality of blood vessels are segmented. The masking of the plurality of blood vessels enables accurate segmentation of the blood vessels without including background image information. The segmentation of the plurality of blood vessels may be performed using one or more techniques well known in the art. At act 504, a virtual model of the plurality of the blood vessels is generated from the segmented plurality of blood vessels. The virtual model may be a 3-dimensional representation of the segmented blood vessels associated with the myocardium region. The virtual model is the simulation of the plurality of the blood vessels. In one embodiment, the simulation of the blood vessels enables effective identification of the at least one blood vessel that may contribute to the abnormality in the myocardium region.

Figure 6:
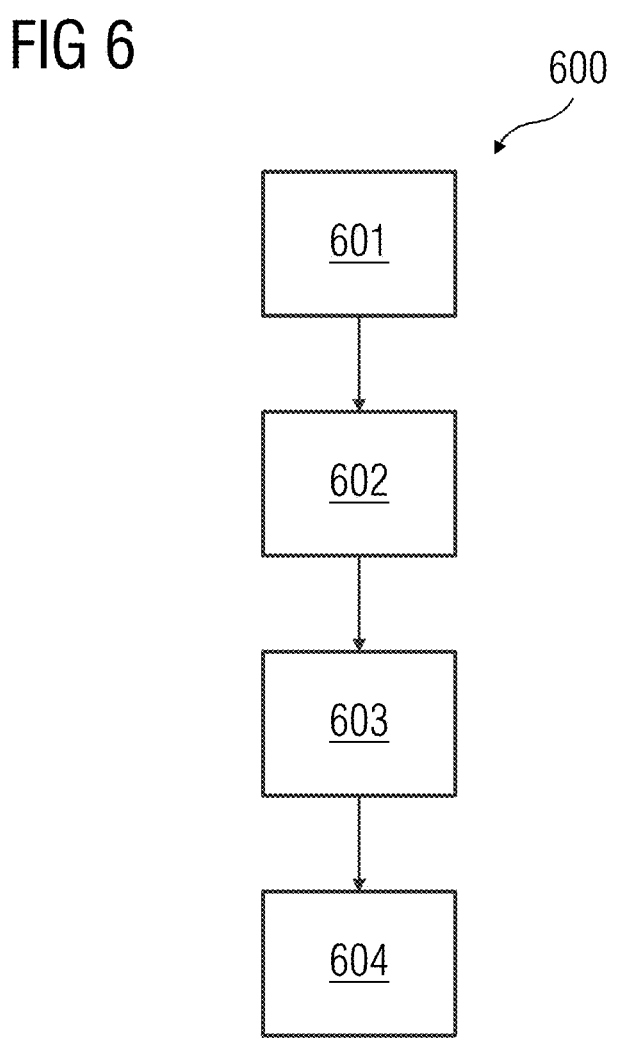

FIG. 6 illustrates a flowchart of a method 600 of determining the at least one blood vessel contributing to the abnormality in the myocardium region. At act 601, the simulated plurality of blood vessels is obtained. At act 602, the medical data associated with the myocardium region is received from the medical database 102. At act 603, a comparison is made between the simulated blood vessels and the medical data associated with the myocardium region. The comparison enables identification of the at least one blood vessel contributing to the abnormality in the myocardium region. At act 604, the at least one blood vessel connecting to the region of abnormality in the myocardium region is identified. In an embodiment, the at least one blood vessel contributing to the abnormality may be depicted in a different color over the other blood vessels. For example, an enhanced mask may be applied to the at least one blood vessel contributing to the abnormality.

The advantage of the present embodiments is that the blood vessel contributing to the abnormality in the myocardium region may be effectively identified. Additionally, manual effort in identifying the contributing blood vessel is avoided. Further, erroneous detection of the contributing blood vessel is prevented.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular devices, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto, and changes may be made without departing from the scope and spirit of the invention in its aspects.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

What is claimed is:

1. A method of determining at least one blood vessel contributing to an abnormality in a myocardium region of a patient, the method comprising:

receiving from a medical imaging device a medical image associated with the myocardium region of the patient;

identifying from the medical image a region of abnormality in the myocardium region of the patient;

generating a simulation of a three-dimensional virtual model of a plurality of blood vessels associated with a myocardium region of one or more other patients, the three-dimensional virtual model being based on medical data associated with the myocardium region of the one or more other patients, the medical data being obtained by the medical imaging device from a medical database; and determining, from the simulation of the three-dimensional virtual model of the plurality of blood vessels associated with the myocardium region of the one or more other patients, at least one blood vessel contributing to the abnormality in the myocardium region of the patient, wherein the at least one blood vessel is associated with the region of abnormality in the myocardium region of the patient, wherein generating the simulation of the three-dimensional virtual model of the plurality of blood vessels comprises:

determining the plurality of blood vessels associated with the myocardium region of the one or more other patients from the medical data associated with the myocardium region of the one or more other patients; and generating the three-dimensional virtual model of the plurality of blood vessels associated with the myocardium region of the one or more other patients, and wherein the medical data associated with the myocardium region of the one or more other patients is further associated with nomenclature and segmentation information associated with the myocardium region and the plurality of blood vessels.

2. The method of claim 1, wherein identifying the region of abnormality in the myocardium region of the patient comprises:

obtaining from the medical database the medical data associated with the myocardium region of the one or more other patients;

determining from the medical image a point of abnormality;

mapping the point of abnormality in the medical image with the medical data associated with the myocardium region of the one or more other patients; and identifying the region of abnormality in the myocardium region of the patient based on the mapping.

3. The method of claim 1, wherein generating the simulation of the three-dimensional virtual model of the plurality of blood vessels further comprises:

generating a mask overlay on the plurality of blood vessels; and segmenting the masked plurality of blood vessels for generation of the three- dimensional virtual model of the plurality of blood vessels.

4. The method of claim 1, further comprising:

determining a centerline associated with each blood vessel of the plurality of blood vessels;

identifying a distal end of the centerline associated with each blood vessel of the plurality of blood vessels;

generating one or more voxels originating from the distal end of the centerline of each vessel of the plurality of blood vessels; and generating an updated three-dimensional virtual model of the plurality of blood vessels based on the generated one or more voxels.

5. The method of claim 1, wherein a proximal end of the simulation of the three-dimensional virtual model of the plurality of blood vessels connect to the myocardium region identified from the medical image.

6. The method of claim 1, wherein determining the at least one blood vessel contributing to the abnormality in the myocardium region of the patient comprises:

comparing the medical data associated with the myocardium region of the one or more other patients with the simulation of the three-dimensional virtual model of the plurality of blood vessels; and determining from the comparison the at least one blood vessel connecting to the region of abnormality in the myocardium region of the patient.

7. The method of claim 1, wherein the medical image is a 3-dimensional medical image.

8. The method of claim 1, wherein the medical image is a computed tomography image, an X-ray fluoroscopic image, a magnetic resonance imaging based image, an ultrasound image, or any combination thereof.

9. A medical imaging device for determining at least one blood vessel contributing to an abnormality in a myocardium region of a patient, the medical imaging device comprising:

one or more processing units;

a scanner unit configured to capture one or more medical images; and a memory coupled to the one or more processing units, the memory comprising a module configured to:

receive from a medical imaging device a medical image associated with the myocardium region of the patient;

identify from the medical image a region of abnormality in the myocardium region of the patient;

generate a simulation of a three-dimensional virtual model of a plurality of blood vessels associated with a myocardium region of one or more other patients, the three-dimensional virtual model being based on medical data associated with the myocardium region of the one or more other patients, the medical data being obtained by the medical imaging device from a medical database; and determine, from the simulation of the three-dimensional virtual model of the plurality of blood vessels, at least one blood vessel contributing to the abnormality in the myocardium region of the patient, wherein the at least one blood vessel is associated with the region of abnormality in the myocardium region of the patient, wherein the generation of the simulation of the three- dimensional virtual model of the plurality of blood vessels comprises:

determination of the plurality of blood vessels associated with the myocardium region of the one or more other patients from the medical data associated with the myocardium region of the one or more other patients; and generation of the three-dimensional virtual model of the plurality of blood vessels associated with the myocardium region of the one or more other patients, and wherein the medical data associated with the myocardium region of the one or more other patients is further associated with nomenclature and segmentation information associated with the myocardium region and the plurality of blood vessels.

10. A system for determining at least one blood vessel contributing to an abnormality in a myocardium region of a patient, the system comprising:

one or more servers; and a medical imaging device coupled to the one or more servers, wherein the one or more servers comprise one or more instructions that, when executed, cause the one or more servers to:

receive from a medical imaging device a medical image associated with the myocardium region of the patient;

identify from the medical image a region of abnormality in the myocardium region of the patient;

generate a simulation of a three-dimensional virtual model of a plurality of blood vessels associated with a myocardium region of one or more other patients, the three-dimensional virtual model being based on medical data associated with the myocardium region of the one or more other patients, the medical data being obtained by the medical imaging device from a medical database; and determine, from the simulation of the three-dimensional virtual model of the plurality of blood vessels, at least one blood vessel contributing to the abnormality in the myocardium region of the patient, wherein the at least one blood vessel is associated with the region of abnormality in the myocardium region of the patient, wherein the generation of the simulation of the three-dimensional virtual model of the plurality of blood vessels comprises:

determination of the plurality of blood vessels associated with the myocardium region of the one or more other patients from the medical data associated with the myocardium region of the one or more other patients; and generation of the three-dimensional virtual model of the plurality of blood vessels associated with the myocardium region of the one or more other patients, and wherein the medical data associated with the myocardium region of the one or more other patients is further associated with nomenclature and segmentation information associated with the myocardium region and the plurality of blood vessels.

11. A non-transitory computer-readable storage medium that stores machine readable instructions executable by a processing unit to determine at least one blood vessel contributing to an abnormality in a myocardium region of a patient, the computer readable instructions comprising:

receiving from a medical imaging device a medical image associated with the myocardium region of the patient;

identifying from the medical image a region of abnormality in the myocardium region of the patient;

generating a simulation of a three-dimensional virtual model of a plurality of blood vessels associated with a myocardium region of one or more other patients, the three-dimensional virtual model being based on medical data associated with the myocardium region of the one or more other patients, the medical data being obtained by the medical imaging device from a medical database; and determining, from the simulation of the three-dimensional virtual model of the plurality of blood vessels, at least one blood vessel contributing to the abnormality in the myocardium region of the patient, wherein the at least one blood vessel is associated with the region of abnormality in the myocardium region of the patient, wherein generating the simulation of the three-dimensional virtual model of the plurality of blood vessels comprises:

determining the plurality of blood vessels associated with the myocardium region of the one or more other patients from the medical data associated with the myocardium region of the one or more other patients; and generating the three-dimensional virtual model of the plurality of blood vessels associated with the myocardium region of the one or more other patients, and wherein the medical data associated with the myocardium region of the one or more other patients is further associated with nomenclature and segmentation information associated with the myocardium region and the plurality of blood vessels.

12. The non-transitory computer-readable storage medium of claim 11, wherein identifying the region of abnormality in the myocardium region of the patient comprises:

obtaining from the medical database the medical data associated with the myocardium region of the one or more other patients;

determining from the medical image a point of abnormality;

mapping the point of abnormality in the medical image with the medical data associated with the myocardium region of the one or more other patients; and identifying the region of abnormality in the myocardium region of the patient based on the mapping.

13. The non-transitory computer-readable storage medium of claim 11, wherein generating the simulation of the three-dimensional virtual model of the plurality of blood vessels further comprises:

generating a mask overlay on the plurality of blood vessels; and segmenting the masked plurality of blood vessels for generation of the three-dimensional virtual model of the plurality of blood vessels.

14. The non-transitory computer-readable storage medium of claim 11, wherein the computer readable instructions further comprise:

determining a centerline associated with each blood vessel of the plurality of blood vessels;

identifying a distal end of the centerline associated with each blood vessel of the plurality of blood vessels;

generating one or more voxels originating from the distal end of the centerline of each vessel of the plurality of blood vessels; and generating an updated three-dimensional virtual model of the plurality of blood vessels based on the generated one or more voxels.

15. The non-transitory computer-readable storage medium of claim 11, wherein a proximal end of the simulation of the three-dimensional virtual model of the plurality of blood vessels connect to the myocardium region identified from the medical image.

16. The non-transitory computer-readable storage medium of claim 11, wherein determining the at least one blood vessel contributing to the abnormality in the myocardium region of the patient comprises:

comparing the medical data associated with the myocardium region of the one or more other patients with the simulation of the three-dimensional virtual model of the plurality of blood vessels; and determining from the comparison the at least one blood vessel connecting to the region of abnormality in the myocardium region of the patient.

17. The non-transitory computer-readable storage medium of claim 11, wherein the medical image is a 3-dimensional medical image.

18. The non-transitory computer-readable storage medium of claim 11, wherein the medical image is a computed tomography image, an X-ray fluoroscopic image, a magnetic resonance imaging based image, an ultrasound image, or any combination thereof.

* * * * *